United States Patent
Hauswald

(10) Patent No.: US 9,744,292 B2
(45) Date of Patent: Aug. 29, 2017

(54) INFUSION DEVICE

(71) Applicant: STC.UNM, Albuquerque, NM (US)

(72) Inventor: Mark Hauswald, Telluride, CO (US)

(73) Assignee: STC.UNM, Albuquerque, NM (US)

( * ) Notice: Subject to any disclaimer, the term of this patent is extended or adjusted under 35 U.S.C. 154(b) by 124 days.

(21) Appl. No.: 14/544,032

(22) Filed: Nov. 17, 2014

(65) Prior Publication Data

US 2015/0141957 A1    May 21, 2015

Related U.S. Application Data

(63) Continuation-in-part of application No. 13/815,405, filed on Feb. 28, 2013, now Pat. No. 8,920,382.

(60) Provisional application No. 61/607,832, filed on Mar. 7, 2012.

(51) Int. Cl.
| | |
|---|---|
| *A61M 5/14* | (2006.01) |
| *A61M 5/142* | (2006.01) |
| *A61M 5/315* | (2006.01) |
| *A61M 5/168* | (2006.01) |

(52) U.S. Cl.
CPC .... *A61M 5/14216* (2013.01); *A61M 5/31548* (2013.01); *A61M 5/1422* (2013.01); *A61M 5/16809* (2013.01); *A61M 5/31535* (2013.01); *A61M 2202/048* (2013.01)

(58) Field of Classification Search
CPC .. A61M 2005/1405; A61M 2005/3115; A61M 5/1424; A61M 5/3158
See application file for complete search history.

(56) References Cited

U.S. PATENT DOCUMENTS

| | | | |
|---|---|---|---|
| 6,270,481 B1 | 8/2001 | Mason et al. | 604/181 |
| 6,719,728 B2 * | 4/2004 | Mason | A61M 5/1424 |
| | | | 604/131 |
| 7,458,956 B1 | 12/2008 | Adams et al. | |
| 8,016,790 B2 | 9/2011 | Walborn et al. | 604/153 |
| 8,308,457 B2 | 11/2012 | Ori Goldor | 417/479 |
| 8,961,462 B2 | 2/2015 | Mernoe | |
| 2007/0299408 A1 | 12/2007 | Alferness et al. | 604/250 |
| 2011/0184348 A1 * | 7/2011 | Bates | A61M 5/14216 |
| | | | 604/131 |

* cited by examiner

*Primary Examiner* — Kevin C Sirmons
*Assistant Examiner* — Deanna K Hall

(57) ABSTRACT

A mechanical infusion pump device for injecting medication into a patient's IV, includes an IV reservoir and a syringe communicated to the IV reservoir and having a syringe plunger which is moved in a first direction against a mechanical biasing element by engagement with a manually operable, independently movable filling plunger to fill the syringe with fluid medication. The mechanical biasing element is provided for exerting bias on the syringe plunger in a second syringe-discharging direction to dispense medication from the syringe into the patient's IV when the filling plunger is released. Only a calibrated amount of medicine can be discharged to the patent's IV over time as determined by calibration of the biasing element and a metering element located between the syringe and the patient's IV for a given viscosity of the medication.

12 Claims, 3 Drawing Sheets

INFUSION DEVICE

RELATED APPLICATION

This application is a continuation-in-part of U.S. application Ser. No. 13/815,405 filed Feb. 28, 2013, which claims benefits and priority of U.S. provisional application Ser. No. 61/607,832 filed Mar. 7, 2012, the entire disclosures of both of which are incorporated herein by reference.

FIELD OF THE INVENTION

This invention relates generally to an infusion pump device and, more specifically, to a mechanical, low cost, and disposable infusion pump device that meters a controlled amount of medication per unit of time to a patient.

BACKGROUND OF THE INVENTION

A problem for critical care medical treatment in the developing world and during transport of patients is that available infusion pumps are expensive, fragile, and require electricity to operate. The alternative to an infusion pump is for the caregiver to watch and count drips in an IV chamber. However, this technique is inaccurate and hence risky. For obstetricians and midwives, oxytocin infusions during difficult birthing (labor) present problems in particular, because the only alternative may be performance of a C-section.

SUMMARY OF THE INVENTION

To this end, the present invention provides an infusion device, especially for use for birthing, critical care or emergency patients, although the invention is not limited to any particular patient use. In an illustrative embodiment of the present invention, infusion pump device comprises an IV medication reservoir, a syringe communicated to the IV medication reservoir and having a syringe plunger movable in a first syringe-filling direction, a filling plunger operable by an individual to engage and move the syringe plunger in the first direction against a biasing element wherein the biasing element exerts bias on the syringe plunger when the syringe is filled to move it in a second syringe-discharging direction to dispense an amount of medication per unit of time to a patient's IV. The filling plunger is movable independently of the syringe plunger and is engaged with but unconnected to the syringe plunger when the filling plunger is moved in the first direction to fill the syringe. Release of the filling plunger permits the biasing element to move the syringe plunger in the second direction to dispense medication.

In a particular embodiment of the present invention, the syringe is communicated to the patient's IV by a metering element that, together with the biasing element, is/are calibrated to allow discharge of a calibrated amount of medication per unit of time. One-way valves are provided between the IV medication reservoir and the syringe and between syringe and the patient's IV to permit the drawing of medication from the IV reservoir into the syringe and dispensing of the medication to the patient's IV.

The present invention also envisions a method of injecting medication into a patient's IV comprising the steps of drawing medication from an IV medication reservoir into a syringe by manually moving the filling plunger to engage and move the syringe plunger in a first syringe-filling direction to fill the syringe and then using the biasing element to exert bias on the plunger of the syringe in a second, syringe-discharging direction to dispense a calibrated amount of medication over time into the patient's IV when the filling plunger is released In an alternate embodiment of the invention when only small quantities of medication are needed, the syringe can be preloaded with the desired quantity that is discharged into the patient's IV bag using the biasing element without the need for use of the filling plunger, IV medication reservoir, and the one-way valve associated with the IV medication reservoir and then the medication is dispensed into the patient's IV bag using the bias of the biasing element.

The infusion pump device and method pursuant to the present invention are advantageous especially for use for the birthing or critical care patient. The device and method provide quick and easy set-up and use.

These and other advantages will become more apparent from the following detailed description taken with the following drawings.

DETAILED DESCRIPTION OF THE INVENTION

Figure 1A:
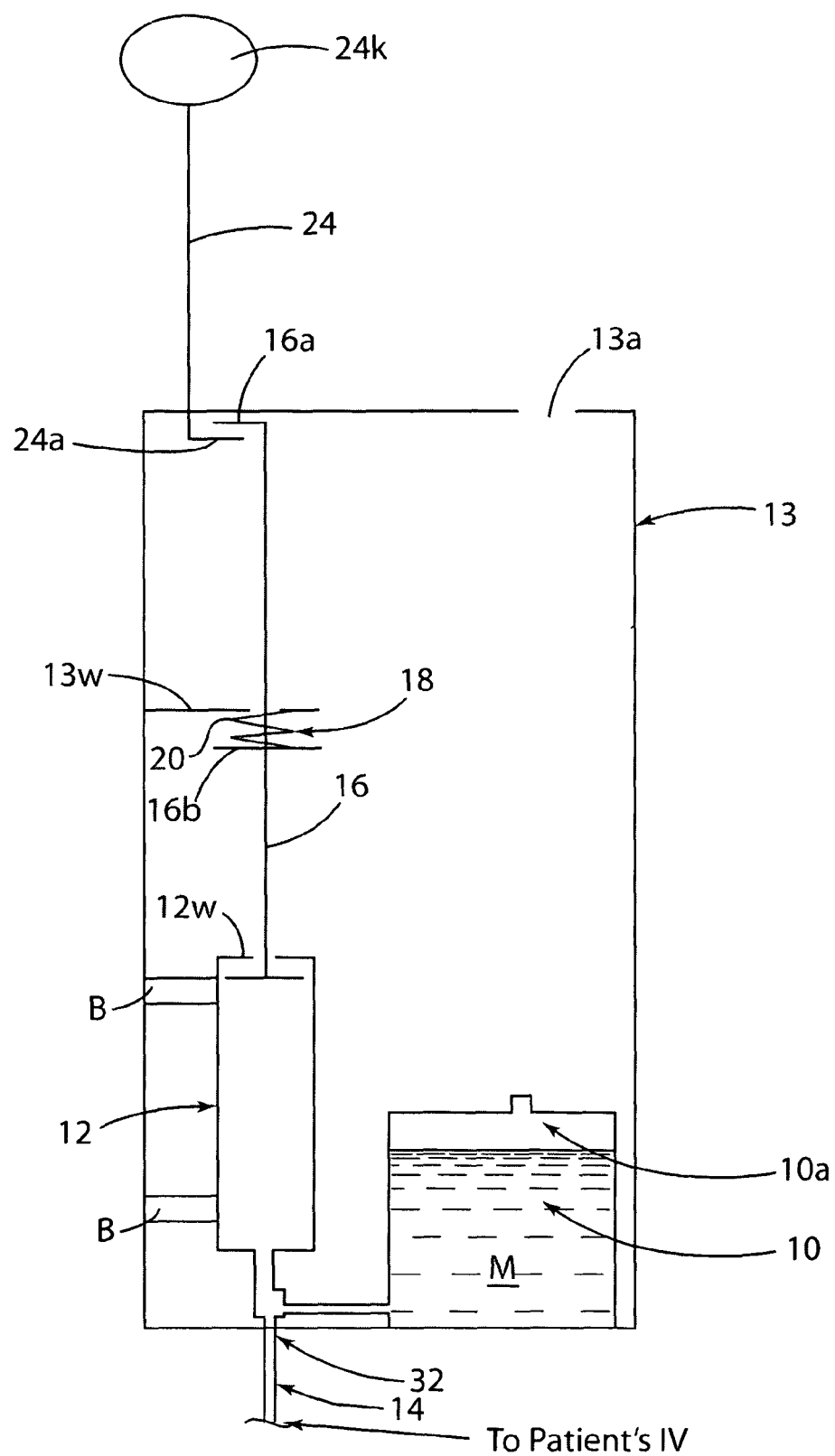
FIGS. 1A and 1B schematically show an illustrative embodiment of a mechanical infusion pump device according to an illustrative embodiment of the present invention wherein FIG. 1A the biasing element is shown compressed and in FIG. 1B is shown extended.
Figure 1B:
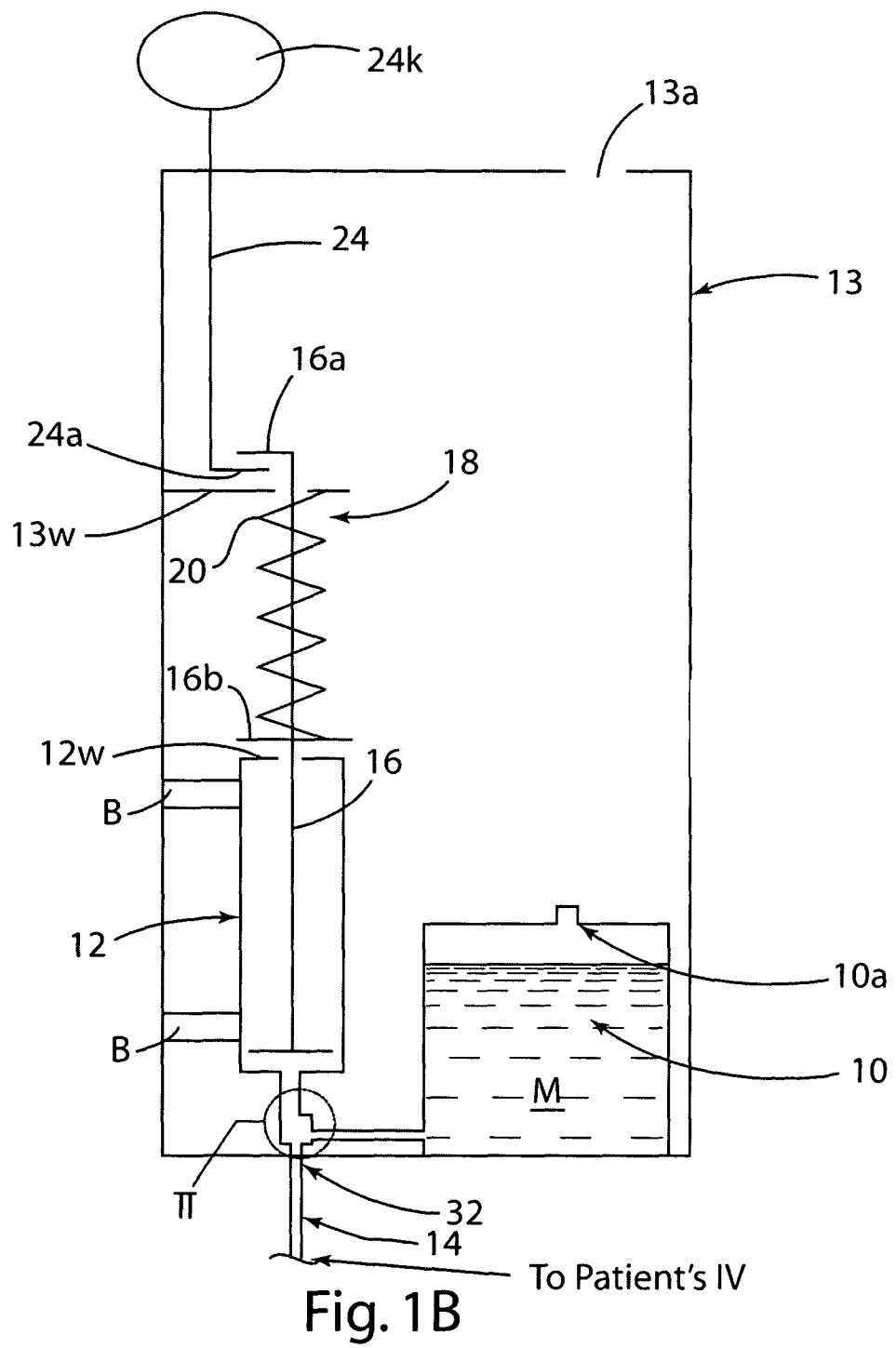
Figure 2:
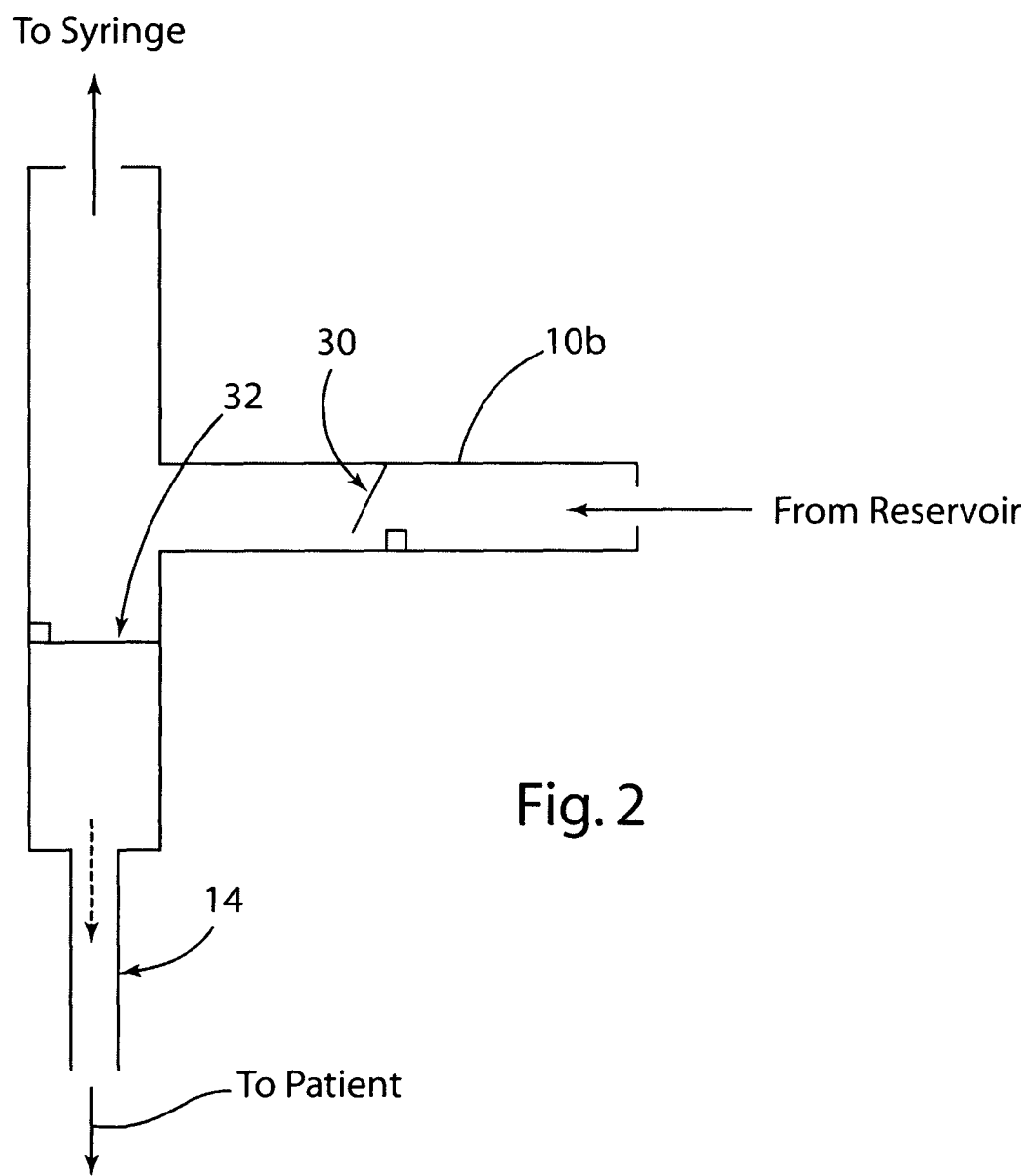
FIG. 2 is an enlarged schematic view of the IV medication reservoir metering element and one-way valves when fluid/medication is being drawn from the reservoir into the syringe (valve from reservoir is open and valve to patient is closed).

FIGS. 1A, 1B and 2 schematically depict an illustrative embodiment of the mechanical infusion pump offered for purposes of illustration and not limitation as comprising a medication reservoir 10, such as, for example, a conventional IV medication bag, and a syringe 12 communicated to the IV bag 10 by the valves in FIG. 2. The IV bag 10 is disposed in the container 13 and shown supported on the container bottom for purposes of illustration and not limitation. The syringe 12 is disposed in the container 13 and is fixedly supported by brackets B or other support in container 13. The container 13 includes an opening 13a that allows ambient air to flow into and out of container 13 and a closeable door (not shown).

The IV reservoir 10 is filled via injection port 10a with medication or is preloaded with medication. The container door can be latched shut after a preloaded bag is in position or after medication is added to the IV bag in the container. For purposes of illustration and not limitation, the IV reservoir 10 can be a commercially available IV bag.

The IV medication reservoir 10 includes or is connected to a one-way valve element 30, which is open when fluid medication is being drawn from the IV reservoir 10 into the syringe 12 and is closed when medication is discharged under pressure to the patient's IV as described below.

The syringe 12 includes syringe plunger 16 which is movable upwardly in FIG. 1A in a first syringe-filling direction to draw fluid medication from the IV reservoir 10 into the syringe. The syringe plunger is moved upwardly by a manually operable filling plunger 24 that is movable independently of the syringe plunger 16 and is engaged with but unconnected to the syringe plunger 16 when the filling plunger is moved in the first direction to fill the syringe.

The filling plunger 24 is located above the syringe plunger 16 and includes a flange 24a that engages flange 16a of the syringe plunger 16 when the filling plunger 24 is pulled upwardly by an individual, such as a patient, nurse, doctor, etc. using the plunger knob 24k shown. The releasable engagement between the upper flange 16a and lower flange 24a prevents pressing of the filling plunger 24 by the individual (e.g. patient) from injecting the medication into the patient's intravenous line. For purposes of illustration and not limitation, the syringe 12 with plunger 16 can be a commercially available syringe modified to include a second flange 16b that is spaced from inner wall shoulder 13w of the container 13 wherein the second flange 16b can be integral or connected to the syringe plunger 16.

When the syringe is filled with medication by pulling of the filling plunger 24 as described above, the syringe plunger 16 is biased by a biasing element 18 that is compressed by virtue of being disposed between the syringe plunger flange 16b and fixed container wall 13w and exerts a bias on the syringe plunger 16 in the second (downward) syringe-discharging direction to dispense a calibrated amount of fluid medication to the patient's IV over a unit of time when the filling plunger 24 is released whereby the filling plunger 24 drops downwardly by gravity or under the influence of the biasing element.

For purposes of illustration, the biasing element 18 is shown comprising a compression coil spring 20, which resides around the shaft of the syringe plunger 16 and between the inner-projecting fixed wall 13w of the container 13 and the flange 16b of the syringe plunger 16 as depicted in FIG. 1A such that upward pulling of the filling plunger 24 and thus the syringe plunger 16 in the first direction compresses the biasing element. The fixed wall 13w is integral to or fixedly connected to the container 13. The coil spring is shown fully compressed in FIG. 1A and extended in FIG. 1B. The biasing element 18 is not limited to a compression spring and can comprise an elastic or resilient plastic or rubber sleeve, or other biasing element that can exert a downward bias on the syringe plunger 16 in FIG. 1A, 1B. The top wall 12w of the syringe includes an opening to allow up/down movement of the syringe plunger 16.

A metering element 14 is disposed between the syringe 12 and the patient's IV to participate in flow rate control of the medication discharged from the syringe 12 into the patient's IV as explained below. For purposes of illustration and not limitation, the metering element 14 can comprise, but is not limited to, a capillary tube, a metering needle valve, or a combination thereof.

The mechanical properties of metering element 14 (e.g. capillary tube radius) and the biasing element 18 (e.g. spring height and strength) are calibrated to permit a calibrated amount of fluid medication to be discharged from the syringe 12 into the patient's IV for a given time (e.g. 6 ml in 60 minutes) corresponding to a maximum amount of medication ordered per unit of time.

A second one-way valve 32 is provided between the syringe 12 and the patient's IV and allows the syringe plunger 16 to push fluid medication from the syringe 12 into patient's IV, but prevents back-flow of IV fluid medication from the patient's IV into the syringe. FIG. 2 illustrates schematically, one-way flapper valves 30 and 32 and a capillary tube type of metering element 14. The one-way valves 30, 32 can include, but are not limited to, ball check valves, conical check valves, or flapper valves.

In practice of a method embodiment of the present invention, the IV medication reservoir 10 is filled via injection port 10a with fluid medication and injection fluid as needed (collectively designated M in FIG. 1A), the IV bag being connected to syringe 12 via tube 10b and one-way valve 30. The door of box or container 13 is closed and locked.

The syringe 12 is filled by the syringe plunger 16 being moved upwardly in FIG. 1A by manual upward pulling of the filling plunger 24 by the individual patient or caregiver until the syringe is filled with the fluid medication.

The filling plunger 24 then is released such that the syringe plunger 16 is moved by the biasing element 18 extending as shown in FIG. 1B to discharge medication to the patient's IV. The medication cannot be discharged to the patient's IV more rapidly than the biasing element 18 (spring 20) and restricting needle or capillary tube metering element 14 allow for a given fluid viscosity of the medication. The patient's inadvertent pressing on the filling plunger 24 will not cause injection of the medication as explained above due to the flanges 24a and 16a becoming disengaged.

The biasing element 18 (e.g. compression spring 20) and metering element 14 (e.g. capillary tube) are calibrated to allow a specific amount of medication to flow out of the syringe 12 per unit time (e.g., 6 ml in 60 minutes), corresponding to a maximum amount of medication ordered per unit time. Different metering elements and biasing elements can be designed to give different volumes of fluid over time with each injection with the metering element and the biasing element being calibrated for each desired application to this end.

Thus, the mechanical properties of the illustrated device (e.g. spring properties and capillary tube radius for a given fluid viscosity) limit the dose per time interval. In particular, the difference between the height of the spring biasing element 20 when fully compressed and the height of the spring biasing element 20 when fully extended for a given capillary metering tube radius determines the maximum amount of medication discharged from the syringe 12, and hence the maximum dose injected at one time. A different spring/metering element (restrictor) combination can be selected and used in order to adjust the particular volume of fluid/medication for each injection. The biasing element 18 (e.g. spring 20) and metering element (restrictor) 14 are calibrated for each combination. A set of calibrated tubes or valves 14 can be provided and connected so that the tubes or valves 14 can be operational in sequence to allow the operator to increase the dose as needed.

Since the viscosity of water soluble medications approximates that of water, a single biasing element and metering element (restrictor) combination can be used for multiple medications.

Moreover, in an alternate embodiment of the invention when only small quantities of medication are needed, the syringe 12 can be preloaded with the desired quantity of medication that is discharged into the patient's IV line using the biasing element 18 without the need for use of the filling plunger 24, IV medication reservoir 10, and the one-way valve 30 associated with the IV medication reservoir 10. In practicing this method, a quantity of medication is preloaded into the syringe 12 in the usual way by pulling the syringe plunger 16 to an extended position out of the syringe to this end. The preloaded syringe is placed in the container 13 so as to be held in fixed position therein by brackets B with the biasing element 18 compressed. The brackets B can be of a type that are openable/closeable to this end. When the syringe plunger 16 is released, the biasing element 18 biases the syringe plunger 16 in the downward syringe-discharging direction of the filled syringe 12 to dispense a controlled amount of medication into the patient's IV over a unit of time as controlled by the biasing element 18 and the metering element 14, which are calibrated to this end as described above.

The infusion pump device described above may be fabricated of conventional medical parts (syringe, restricting needle, connecting tubing, valves and IV medication bag), but using components specifically designed for the device could make it simpler and easier to set up. The device thus can be very low cost and hence disposable. The above-described embodiments of the device do not comprise any electrical or electro-mechanical parts, although such parts may be incorporated into the device. For example, the biasing element 18 may be replaced by an electrical or electromechanical (solenoid) biasing element.

The device has potential uses in pre-hospital (ambulance) care, acute/urgent care clinics, birthing clinics, emergency departments, intensive care units and other sites where infusions of medications are needed.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention within the scope of the appended claims. Other embodiments will be apparent to those skilled in the art from consideration of the specification and practice of the embodiments disclosed herein. It is intended that the specification and examples be considered as examples only.

I claim:

1. An infusion device, comprising an IV medication reservoir, a syringe communicated to the IV medication reservoir and having a syringe plunger movable in a first syringe-filling direction, a filling plunger manually operable by an individual to engage the syringe plunger in a common housing and move the syringe plunger in the first syringe-filling direction to fill the syringe with medication and is movable independently of and unconnected to the syringe plunger when the filling plunger is manually moved in an opposite second syringe-discharging direction in the syringe housing after the syringe is filled, whereby medication cannot be inadvertently discharged from the syringe to the patient's IV by manually moving the filling plunger in the second syringe-discharging direction, and a biasing element for exerting bias on the syringe plunger when the syringe is filled and the filling plunger is manually released to move the syringe plunger in the second syringe-discharging direction to dispense an amount of medication per unit of time to a patient's IV.

2. The device of claim 1 including said biasing element and a metering element between the syringe and the patient's IV to provide a specific amount of medication to flow out of the syringe per unit time.

3. The device of claim 1 further including a one-way valve to prevent medication from being transferred from the syringe back into the IV medication reservoir when the syringe plunger is moved in the second direction.

4. The device of claim 1 further including a second one-way valve to prevent flow of medication from the patient's IV back to the syringe when the syringe plunger is moved in the first direction.

5. The device of claim 1 wherein the filling plunger includes a manually operable outer end used to manually move the syringe plunger in the first syringe-filling direction.

6. The device of claim 1 wherein the biasing element is disposed between a fixed wall that is spaced from a flange of the syringe plunger.

7. The device of claim 1 wherein the biasing element is a compression spring.

8. The device of claim 1 further including a container in which the IV medication reservoir, the syringe, and the biasing element are enclosed.

9. The device of claim 7 wherein the container includes an opening to admit air into the container.

10. A method of injecting medication into a patient's IV, comprising drawing medication from an IV medication reservoir into a syringe by manually moving a filling plunger in a first syringe-filling direction against a biasing element while the filling plunger engages but is unconnected to a syringe plunger in a common syringe housing to fill the syringe with medication wherein after the syringe is filled, the medication cannot be discharged from the syringe by manually moving the filling plunger in the second syringe-discharging direction, and using the biasing element to exert a bias on the syringe plunger in the second syringe-discharging direction when the syringe is filled and the filling plunger is manually released to dispense a controlled amount of medication into the patient's IV over a unit of time.

11. The method of claim 10 wherein the individual pulls the filling plunger in the first syringe-filling direction to engage and move the syringe plunger against the bias of the biasing element.

12. The method of claim 10 including calibrating said biasing element and a metering element located between the syringe and the patient's IV to provide a specific amount of medication to flow out of the syringe per unit time.

* * * * *